(12) United States Patent
Walton et al.

(10) Patent No.: US 9,068,439 B2
(45) Date of Patent: Jun. 30, 2015

(54) SYSTEMS AND METHODS OF POSITIVE INDICATION OF ACTUATION OF A DOWNHOLE TOOL

(71) Applicants: Zachary W. Walton, Duncan, OK (US); Michael L. Fripp, Carrollton, TX (US)

(72) Inventors: Zachary W. Walton, Duncan, OK (US); Michael L. Fripp, Carrollton, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 142 days.

(21) Appl. No.: 13/770,349

(22) Filed: Feb. 19, 2013

(65) Prior Publication Data

US 2014/0231071 A1   Aug. 21, 2014

(51) Int. Cl.
| | |
|---|---|
| *E21B 47/11* | (2012.01) |
| *E21B 47/10* | (2012.01) |
| *E21B 47/12* | (2012.01) |
| *E21B 47/09* | (2012.01) |
| *E21B 34/00* | (2006.01) |

(52) U.S. Cl.
CPC ........... *E21B 47/1015* (2013.01); *E21B 47/102* (2013.01); *E21B 47/12* (2013.01); *E21B 47/09* (2013.01); *E21B 2034/007* (2013.01)

(58) Field of Classification Search
CPC .............................. E21B 47/10; E21B 47/1015
USPC ........... 166/250.12, 252.6; 436/27; 356/243.2
See application file for complete search history.

(56) References Cited

U.S. PATENT DOCUMENTS

| | | | |
|---|---|---|---|
| 6,125,934 A * | 10/2000 | Lenn et al. ............... | 166/250.12 |
| 6,198,531 B1 | 3/2001 | Myrick et al. | |
| 6,529,276 B1 | 3/2003 | Myrick | |
| 6,799,634 B2 * | 10/2004 | Hartog et al. ............ | 166/250.12 |
| 6,840,316 B2 * | 1/2005 | Vinegar et al. ........... | 166/250.12 |
| 7,424,910 B2 * | 9/2008 | Xu et al. ................... | 166/250.01 |
| 7,770,652 B2 | 8/2010 | Barnett | |
| 8,172,007 B2 * | 5/2012 | Dolman et al. ................. | 175/57 |
| 8,464,581 B2 * | 6/2013 | Rytlewski et al. .......... | 73/152.29 |
| 8,550,103 B2 * | 10/2013 | Chen et al. ........................ | 137/67 |
| 8,567,497 B2 * | 10/2013 | Moen et al. ................ | 166/252.6 |
| 8,833,154 B2 * | 9/2014 | Skillingstad ............... | 73/152.18 |
| 2009/0087911 A1 * | 4/2009 | Ramos ............................ | 436/27 |
| 2009/0087912 A1 * | 4/2009 | Ramos et al. ................... | 436/27 |

(Continued)

FOREIGN PATENT DOCUMENTS

| | | |
|---|---|---|
| WO | 0173423 A1 | 10/2001 |
| WO | 2014130288 A1 | 8/2014 |

OTHER PUBLICATIONS

International Search Report and Written Opinion for PCT/US2014/015681 dated May 20, 2014.

*Primary Examiner* — Kenneth L Thompson
(74) *Attorney, Agent, or Firm* — McDermott Will & Emery LLP; John W. Wustenberg

(57) ABSTRACT

Disclosed are systems and methods of positive indication of the proper actuation of a downhole tool. One system includes a work string providing a flow path therein, a downhole tool coupled to the work string and having a body fluidly coupled to the flow path, an indicator chamber defined in the body and configured to retain a substance therein until the downhole tool is actuated, whereupon the indicator chamber becomes exposed and the substance is released into the flow path, and an optical computing device in optical communication with the flow path and configured to detect a characteristic of the substance in the flow path and communicate a signal when the characteristic is detected, the signal being indicative that the downhole tool has been actuated.

28 Claims, 3 Drawing Sheets

(56) References Cited

U.S. PATENT DOCUMENTS

| | | |
|---|---|---|
| 2009/0151939 A1 | 6/2009 | Bailey et al. |
| 2010/0044041 A1 | 2/2010 | Smith et al. |
| 2010/0245096 A1 | 9/2010 | Jones et al. |
| 2011/0017458 A1 | 1/2011 | East, Jr. et al. |
| 2011/0257887 A1* | 10/2011 | Cooper et al. .................. 702/12 |
| 2011/0277996 A1* | 11/2011 | Cullick et al. ........... 166/250.12 |
| 2013/0020088 A1* | 1/2013 | Dyer et al. .................... 166/373 |
| 2014/0318769 A1* | 10/2014 | Walton et al. ............ 166/250.12 |

\* cited by examiner

SYSTEMS AND METHODS OF POSITIVE INDICATION OF ACTUATION OF A DOWNHOLE TOOL

BACKGROUND

The present disclosure is generally related to wellbore operations and, more particularly, to positive indication of the proper actuation of a downhole tool.

Hydrocarbon-producing wells are often stimulated by hydraulic fracturing operations in order to enhance the production of hydrocarbons present in subterranean formations. During a typical fracturing operation, a servicing fluid (i.e., a fracturing fluid or a perforating fluid) may be injected into a subterranean formation penetrated by a wellbore at a hydraulic pressure sufficient to create or enhance fractures within the subterranean formation. The resulting fractures serve to increase the conductivity potential for extracting hydrocarbons from the subterranean formation.

In some wellbores, it may be desirable to strategically generate multiple fractures along the wellbore at predetermined distances apart from each other, thereby creating multiple "pay zones" in the subterranean formation. Some pay zones may extend a substantial distance along the axial length of the wellbore. In order to adequately fracture the subterranean formation encompassing such pay zones, it may be advantageous to introduce a stimulation fluid via multiple stimulation assemblies arranged within the wellbore at spaced apart locations on a work string extended therein. Each stimulation assembly, commonly referred to as sliding sleeve assemblies, may include, for example, a sliding sleeve configured to be opened and/or shut in order to regulate fluid communication between the interior of the work string and the surrounding subterranean formation.

In some applications, the sleeve may be opened or otherwise actuated by introducing a wellbore projectile, such as a ball or a dart, into the work string. The wellbore projectile is conveyed to the location of the sleeve and engages an internal baffle or seat defined on the interior surface of the work string. Once the wellbore projectile is properly seated on its corresponding internal baffle, the work string is pressurized to a predetermined pressure and the increased pressure serves to actuate the sleeve via a variety of mechanical or hydraulic means. As measured at the surface, the predetermined increased pressure also serves as an indicator that the sleeve has opened or otherwise has been moved as planned.

In some cases, however, the increased pressure in the work string does not actually result in the movement of the sleeve. Instead, the increased pressure can sometimes force the wellbore projectile to extrude past the baffle without actually causing the sleeve to actuate. Nevertheless, in such cases, the increased pressure is measured at the surface and erroneously informs an operator that the sleeve has moved when in reality the sleeve has remained stationary throughout the pressurization process. As a result, subsequent wellbore operations requiring the sleeve to have moved as planned will be ineffective and result in lost time and costs.

SUMMARY OF THE DISCLOSURE

The present disclosure is generally related to wellbore operations and, more particularly, to positive indication of the proper actuation of a downhole tool.

In some embodiments, a well system may be disclosed and may include a work string providing a flow path therein, a downhole tool coupled to the work string and having a body fluidly coupled to the flow path, an indicator chamber defined in the body and configured to retain a substance therein until the downhole tool is actuated, whereupon the indicator chamber becomes exposed and the substance is released into the flow path, and an optical computing device in optical communication with the flow path and configured to detect a characteristic of the substance in the flow path and communicate a signal when the characteristic is detected, the signal being indicative of downhole tool having been actuated.

In other embodiments, a method is disclosed that may include retaining a substance within an indicator chamber defined in a body of a downhole tool, the downhole tool being coupled to a work string that provides a flow path therein, and the body being in fluid communication with the flow path, actuating the downhole tool and thereby exposing the indicator chamber and releasing the substance into the flow path, monitoring the flow path with an optical computing device configured to detect a characteristic of the substance in the flow path, and communicating a signal with the optical computing device when the characteristic of the substance is detected, the signal being indicative that the downhole tool has been actuated.

In yet other embodiments, another well system may be disclosed and may include a work string providing a flow path therein, a sliding sleeve assembly coupled to the work string and having a body with a sleeve movably arranged therein between a closed configuration, where fluid communication is prevented between an interior of the body and an exterior of the work string, and an open configuration, where fluid communication is allowed between the interior of the body and the exterior of the work string, an indicator chamber defined in the body and configured to retain a substance therein when the sleeve is in the closed configuration and release the substance into the flow path when the sleeve is in the open configuration, and an optical computing device in optical communication with the flow path and configured to detect a characteristic of the substance in the flow path and communicate a signal when the characteristic is detected, the signal being indicative that the sleeve is in the open configuration.

In even further embodiments, another method may be disclosed and may include retaining a substance within an indicator chamber defined in a body of a sliding sleeve assembly, the sliding sleeve assembly being coupled to a work string that provides a flow path therein, and the body being in fluid communication with the flow path, moving a sleeve arranged within the body from a closed configuration, where the indicator chamber is occluded and fluid communication is prevented between an interior of the body and an exterior of the work string, and an open configuration, where the indicator chamber is exposed and fluid communication is allowed between the interior of the body and the exterior of the work string, releasing the substance into the flow path from the indicator chamber, monitoring the flow path with an optical computing device configured to detect a characteristic of the substance in the flow path, and communicating a signal with the optical computing device when the characteristic of the substance is detected, the signal being indicative that the sleeve is in the open configuration.

The features of the present disclosure will be readily apparent to those skilled in the art upon a reading of the description of the preferred embodiments that follows.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combina

DETAILED DESCRIPTION

The present disclosure is generally related to wellbore operations and, more particularly, to positive indication of the proper actuation of a downhole tool.

The disclosed systems and methods provide a positive indication to a well operator of the actuation of a downhole tool, such as a sliding sleeve assembly. The downhole tool may include an indicator chamber that houses or otherwise retains a buoyant substance that is detectable at the surface using one or more optical computing devices. When the downhole tool actuates, such as when a sliding sleeve moves from its closed configuration into its open configuration, the indicator chamber may become exposed and the buoyant substance may thereby be released into the work string. Since the substance is buoyant as compared to the fluid already disposed within the work string, it tends to float toward the surface. Once the substance is detected by the optical computing device, a signal may be sent which provides a well operator with a positive indication that the sliding sleeve has indeed moved to the open configuration. At that point, the well operator may confidently perform or otherwise undertake subsequent well operations that require the sliding sleeve to be in the open configuration.

Figure 1:
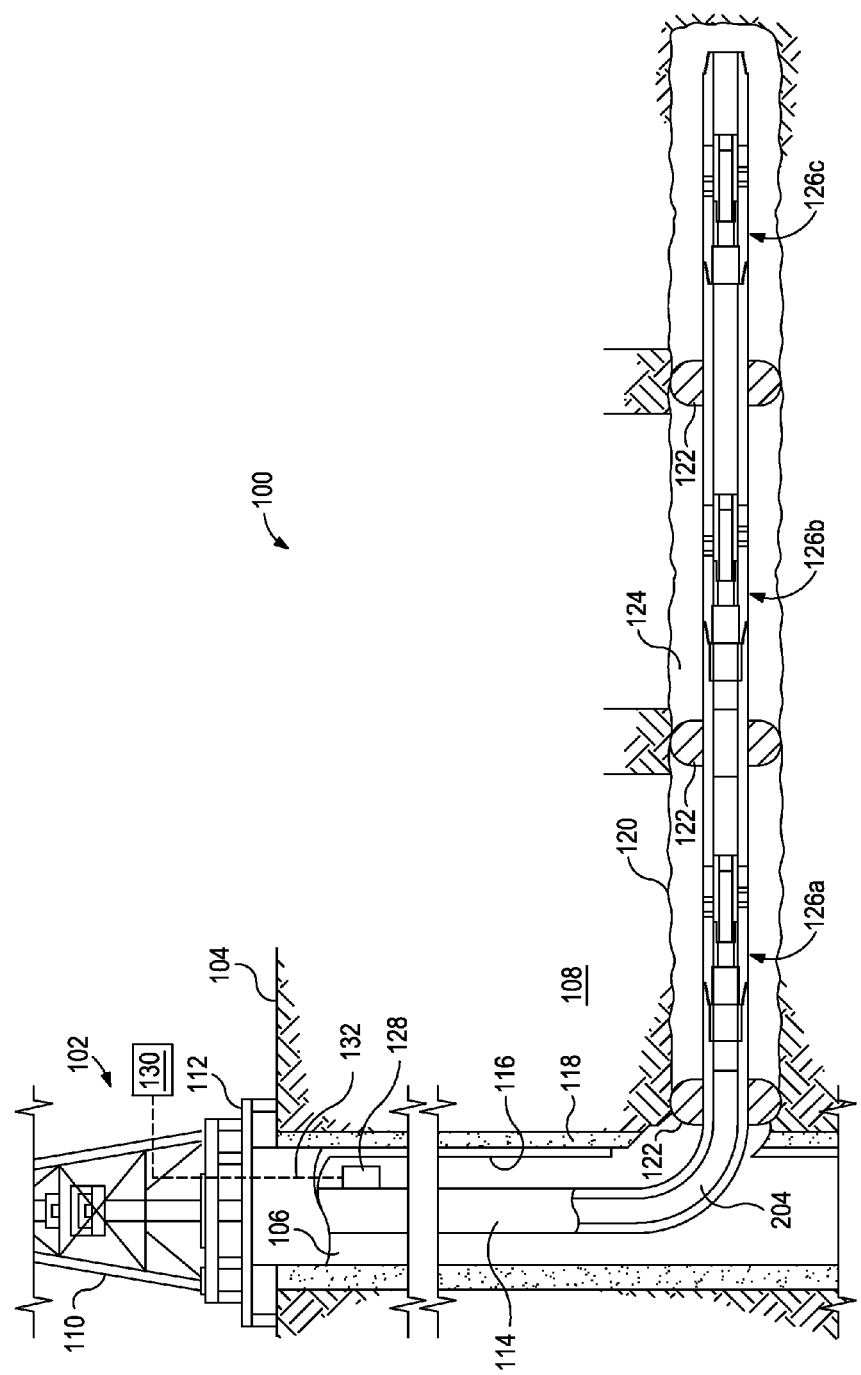
- FIG. 1 is a schematic of an exemplary well system which can embody or otherwise employ one or more principles of the present disclosure, according to one or more embodiments.

Referring to FIG. 1, illustrated is an exemplary well system 100 which can embody or otherwise employ one or more principles of the present disclosure, according to one or more embodiments. As illustrated, the well system 100 may include an oil and gas rig 102 arranged at the Earth's surface 104 and a wellbore 106 extending therefrom and penetrating a subterranean earth formation 108. It should be noted that, even though FIG. 1 depicts a land-based oil and gas rig 102, it will be appreciated that the embodiments of the present disclosure are equally well suited for use in other types of rigs, such as offshore platforms, or rigs used in any other geographical location.

The rig 102 may include a derrick 110 and a rig floor 112, and the derrick 110 may support or otherwise help manipulate the axial position of a work string 114 extended within the wellbore 106 from the rig floor 112. As used herein, the term "work string" refers to one or more types of connected lengths of tubulars as known in the art, and may include, but is not limited to, drill pipe, drill string, landing string, production tubing, casing, liners, combinations thereof, or the like. In other embodiments, the work string 114 may be or otherwise represent any other downhole conveyance means known to those skilled in the art such as, but not limited to, coiled tubing, wireline, slickline, and the like, without departing from the scope of the disclosure. The work string 114 may be connected to the surface 104 and, in at least one embodiment, may have an open hole section between the work string 114 and the surface 104 (such as in a lateral where there is often an open hole section at the junction). In exemplary operation, the work string 114 may be utilized in drilling, stimulating, completing, or otherwise servicing the wellbore 106, or various combinations thereof.

As illustrated, the wellbore 106 may extend substantially vertically away from the surface 104 over a vertical wellbore portion. In other embodiments, the wellbore 106 may otherwise deviate at any angle from the surface 104 over a deviated or horizontal wellbore portion. In other applications, portions or substantially all of the wellbore 106 may be vertical, deviated, horizontal, and/or curved. Moreover, use of directional terms such as above, below, upper, lower, upward, downward, uphole, downhole, and the like are used in relation to the illustrative embodiments as they are depicted in the figures, the upward direction being toward the top of the corresponding figure and the downward direction being toward the bottom of the corresponding figure, the uphole direction being toward the surface of the well and the downhole direction being toward the toe or bottom of the well.

In an embodiment, the wellbore 106 may be at least partially cased with a casing string 116 or may otherwise remain at least partially uncased. The casing string 116 may be secured into position within the wellbore 106 using, for example, cement 118. In other embodiments, the casing string 116 may be only partially cemented within the wellbore 106 or, alternatively, the casing string 116 may be entirely uncemented. A lower portion of the work string 114 may extend into a branch or lateral portion 120 of the wellbore 106. As illustrated, the lateral portion 120 may be an uncased or "open hole" section of the wellbore 106. It is noted that although FIG. 1 depicts horizontal and vertical portions of the wellbore 106, the principles of the apparatuses, systems, and methods disclosed herein may be similarly applicable to or otherwise suitable for use in wholly horizontal or vertical wellbore configurations. Consequently, the horizontal or vertical nature of the wellbore 106 should not be construed as limiting the present disclosure to any particular wellbore 106 configuration.

The work string 114 may be arranged or otherwise seated within the lateral portion 120 of the wellbore 106 using one or more packers 122 or other wellbore isolation devices known to those skilled in the art. The packers 122 may be configured to seal off an annulus 124 defined between the work string 114 and the walls of the wellbore 106. As a result, the subterranean formation 108 may be effectively divided into multiple intervals or "pay zones" which may be stimulated and/or produced independently via isolated portions of the annulus 124 defined between adjacent pairs of packers 122. While only three pay zones are shown in FIG. 1, those skilled in the art will readily recognize that any number of pay zones may be used in the well system 100, without departing from the scope of the disclosure.

The well system 100 may further include one or more downhole tools 126 (shown as 126a, 126b, and 126c) arranged in, coupled to, or otherwise forming an integral part of the work string 114. As illustrated, at least one downhole tool 126 may be arranged in the work string 114 in each pay zone, but those skilled in the art will readily appreciate that more than one downhole tool 126 may be arranged therein, without departing from the scope of the disclosure. The downhole tool 126 may include a variety of tools, devices, or machines known to those skilled in the art that may be used in the preparation, stimulation, and production of the subterranean formation 108. In at least one embodiment, the downhole tool 126 in each pay zone may include or otherwise be a sliding sleeve assembly that may be actuatable in order to provide fluid communication between the annulus 124 and the interior of the work string 114. In other embodiments, the downhole tool 126 may be a fluid collection device, such as a fluid sampler, or a fluid restriction device, such as a valve, inflow control device, autonomous inflow control device, adjustable inflow control device, or the like. In yet other embodiments, the downhole tool 126 may encompass two or more of the above-identified devices, without departing from the scope of the disclosure.

Figure 2A:
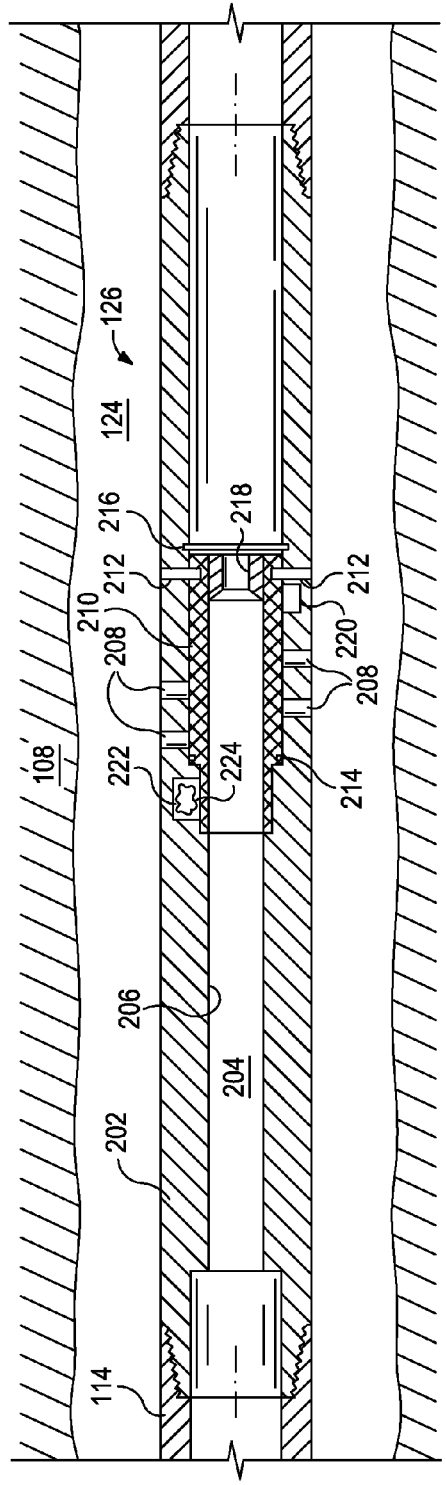
FIGS. 2A and 2B are enlarged cross-sectional views of an exemplary downhole tool, according to one or more embodiments.
Figure 2B:
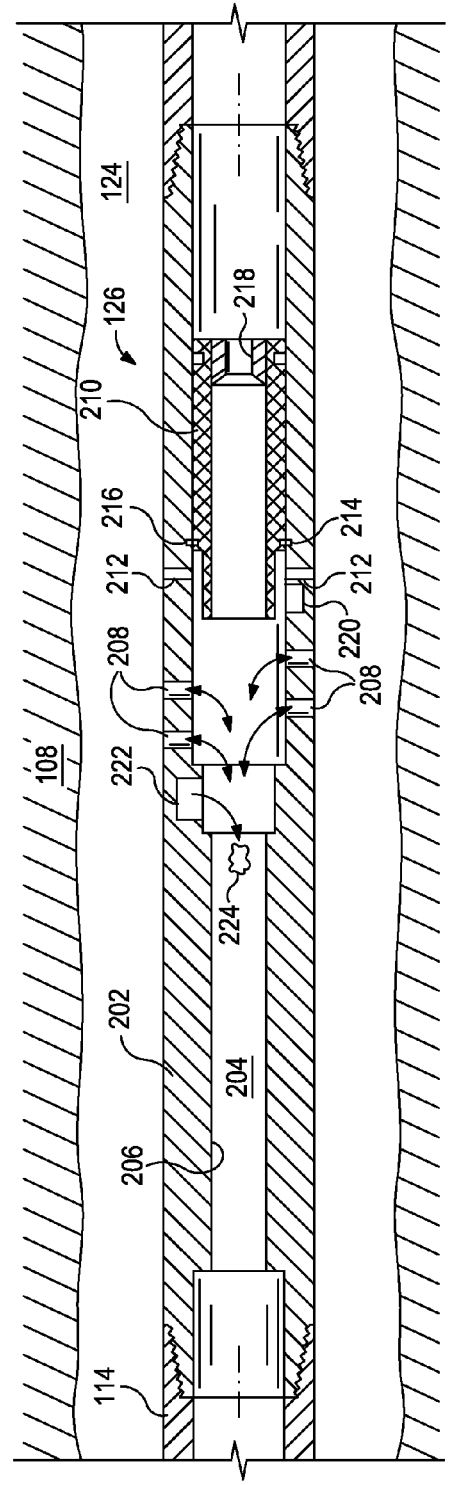

Referring to FIGS. 2A and 2B, with continued reference to FIG. 1, illustrated are enlarged cross-sectional views of an exemplary downhole tool, such as one of the downhole tools 126 of FIG. 1, according to one or more embodiments. In the illustrated embodiment, the downhole tool 126 may be a sliding sleeve assembly that includes an elongate body 202 threaded or otherwise coupled to the work string 114 at opposing ends thereof. The body 202 may define a central passageway in its interior 206 such that a flow path 204 is provided that fluidly connects the work string 114 to the downhole tool 126. The flow path 204 may be configured to extend along the entire length of the work string 114.

The body 202 may also define one or more flow ports 208 configured to provide fluid communication between the annulus 124 and the interior 206 of the work string 114. In some embodiments, the flow ports 208 may be fitted with one or more flow control devices (e.g., nozzles, erodible nozzles, inflow control devices, flow restrictors, etc.). In other embodiments, the flow ports 208 may be fitted with one or more plugs, screens, covers, or shields, for example, to prevent debris from entering the interior 206 of the work string 114.

A sleeve 210 may be slidably or movably arranged within the interior 206 between open and closed configurations. For example, the sleeve 210 is depicted in FIG. 2A in a closed configuration where the sleeve 210 generally occludes the flow ports 208 and thereby prevents fluid communication between the annulus 124 and the interior 206 of the work string 114. FIG. 2B, however, depicts the sleeve 210 in an open configuration where the sleeve 210 has been axially moved within the interior 206 such that the flow ports 208 are exposed and fluid communication between the annulus 124 and the interior 206 is thereby allowed or otherwise facilitated. With the sleeve 210 in the open configuration, various fracturing or stimulation fluids may be discharged from the work string 114 or downhole tool 126 via the flow ports 208 in order to stimulate the surrounding formation 108. Alternatively, with the sleeve 210 in the open configuration, fluids derived from the formation 108 and annulus 124 may be drawn into the work string 114 via the flow ports 208 and produced to the surface 104 (FIG. 1) for processing.

In one or more embodiments, the sleeve 210 may be held in the closed configuration using at least one suitable retaining mechanism, such as one or more frangible members 212. The frangible member 212 may be, for example, a shear pin, a shear ring, or the like, and may be arranged in corresponding bores defined in both the body 202 and the sleeve 210. Upon being subject to or otherwise surpassing a predetermined shear limit, the frangible member(s) 212 may be configured to shear and thereby allow the sleeve 210 to slide axially within the interior 206 to its open configuration, as shown in FIG. 2B.

In the open configuration, in at least one embodiment, the sleeve 210 may be configured to rest against an abutment or a shoulder (not shown) provided or otherwise defined within the body 202 in order to prevent the sleeve 210 from advancing further downhole (e.g., to the right in FIGS. 2A and 2B). In other embodiments, the sleeve 210 may be held in the open configuration using a suitable retaining mechanism, such as a snap ring 214 or the like. The snap ring 214 may be received and/or carried within a groove defined in the sleeve 210 and configured to expand upon locating a complementary groove 216 defined in the body 202. As depicted in FIG. 2B, the snap ring 214 has successfully located the groove 216 in the body 202 and thereby has stopped the axial movement of the sleeve 210 in the downhole direction.

In one or more embodiments, the sleeve 210 may be moved from its closed configuration (FIG. 2A) to its open configuration (FIG. 2B) using one or more wellbore projectiles (not shown) introduced into the work string 114 from the surface and conveyed to the downhole tool 126. Exemplary wellbore projectiles include, but are not limited to, balls, darts, and plugs, as generally known in the art. The sleeve 210 may have or otherwise define a seat or baffle 218 configured to receive, engage, and/or retain a wellbore projectile of a given size and/or configuration. As illustrated, the baffle 218 may exhibit a reduced diameter in comparison to the diameter of the flow path 204 and may therefore be configured to engage and generally prevent the wellbore projectile from advancing any further downhole past the baffle 218. Once the wellbore projectile is properly engaged on or with the baffle 218, fluid communication past the baffle 218 in the downhole direction is substantially prevented, thereby allowing the flow path 204 to be hydraulically pressurized from the surface. Upon pressurizing the flow path 204, the predetermined shear limit of the frangible members 212 may be reached in order to shear the members 212 and allow the sleeve 210 to move axially downhole to its open configuration.

In other embodiments, the sleeve 210 may be shifted and otherwise moved using a shifting tool (not shown), such as a mechanical shifting tool. In such an embodiment, the sleeve 210 may include one or more lugs, dogs, keys, catches, and/or structures complementary to one or more corresponding lugs, dogs, keys, catches, and/or structures of an exemplary shifting tool. Upon properly coupling the shifting tool to the sleeve, force may be applied from the surface and transferred to the sleeve 210 via the shifting tool. Suitable shifting tools are disclosed in U.S. patent application Ser. Nos. 12/358,079 and 12/566,467, each of which is incorporated herein in its entirety.

In yet other embodiments, the downhole tool 126 may further include at least one actuation device 220 operatively coupled to or otherwise forming an integral part of the downhole tool 126. The actuation device 220 may be configured to axially move the sleeve 210 within the interior 206 of the body 202 between the open and closed configurations. The actuation device 220 may include, but is not limited to an electromechanical actuation device such as an electromechanical actuator, a mechanical actuator, a hydraulic actuator, a pneumatic actuator, a piezoelectric actuator, a solenoid, combinations thereof, and the like. In other embodiments, the actuation device 220 may be a motor powered with electrical power, hydraulic fluid pressure, pneumatic pressure, combinations thereof, and the like. Accordingly, in at least one embodiment, the sleeve 210 may be moved back and forth between the open and closed configurations.

In one or more embodiments, the body 202 may further define or otherwise provide an indicator chamber 222. In some embodiments, the indicator chamber 222 may be a radially-extending groove or recess defined in the inner surface of the interior 206. In other embodiments, however, the indicator chamber 222 may be any suitable recess, depression, groove, or divot defined in the inner surface of the interior 206. The indicator chamber 222 may be generally sized, shaped, or otherwise configured to receive and retain a substance 224 when the sleeve 210 is in the closed configuration. Once the sleeve 210 moves from the closed configuration to the open configuration, however, the indicator chamber 222 may become exposed to the interior 206 of the work string 114 and otherwise able to release the substance 224 into the interior 206 and the flow path 204.

As will be described in greater detail below, the substance 224 may be or otherwise include a buoyant fluid or material as compared to the fluid already disposed within the flow path 204. As a result, upon being released from the indicator chamber 222, the substance 224 may be configured to float toward the surface 104 (FIG. 1) within the flow path 204. Once reaching the surface 104, the substance 224 may be detected in order to provide a positive opening indication to a well operator that the sleeve 210 has transitioned from the closed position to the open position. As will be appreciated, knowing that the sleeve 210 has indeed successfully transitioned from the closed position to the open position may allow the well operator to confidently perform subsequent well operations that require the sleeve 210 to be in the open configuration.

Referring again to FIG. 1, with continued reference to FIGS. 2A and 2B, the well system 100 may further include at least one optical computing device 128 arranged within the flow path 204 or otherwise in optical communication with the flow path 204. While only one optical computing device 128 is depicted, it will be appreciated that any number of optical computing devices 128 may be used, without departing from the scope of the disclosure. In some embodiments, the optical computing device 128 may be arranged within the wellbore 106 near the surface 104, as illustrated. In other embodiments, however, the optical computing device 128 may be arranged at the surface 104, such as on the rig 102. In yet other embodiments, the optical computing device 128 may be arranged at any intermediate location within the well system 100 (e.g., between the surface 104 and the downhole tools 126a-c) so long as it remains in optical communication with the flow path 204, without departing from the scope of the disclosure.

As illustrated, the optical computing device 128 may be communicably coupled to a computer system 130 or the like arranged at the surface 104 via one or more communication lines 132. The communication line(s) 132 may be any wired or wireless means of telecommunication between two locations and may include, but is not limited to, electrical lines, fiber optic lines, radio frequency transmission, electromagnetic telemetry, acoustic telemetry, or any other type of telecommunication means known to those skilled in the art. In at least one embodiment, the optical computing device 128 may form an integral part of the computer system 130.

In exemplary operation, the indicator chamber 222 may be configured to retain a predetermined concentration or amount of the substance 224 and the optical computing device 128 may be configured to continuously monitor the flow path 204 for the substance 224 as it floats toward the surface 104 upon being released from the indicator chamber 222. Once the optical computing device 128 detects the substance 224 (or a particular characteristic thereof), it may communicate a signal indicating the same to the computer system 130 via the communication lines 132. A well operator may be able to consult the computer system 130, such as one or more peripheral devices associated therewith (e.g., a monitor, a print out from a printer, an audible or visual alarm, etc.), and thereby become apprised, in real-time, of when the optical computing device 128 affirmatively detects the substance 224 (or a particular characteristic thereof). As a result, the well operator may be provided in real-time with a positive indication that the sleeve 210 has successfully transitioned from the closed position to the open position.

A description of the exemplary optical computing device 128 and its exemplary operation is now provided. As used herein, the term "optical computing device" refers to an optical measurement device configured to receive an input of electromagnetic radiation associated with a substance (i.e., the substance 224) and produce an output of electromagnetic radiation from a processing element arranged within or otherwise forming an integral part of the optical computing device. The processing element may be, for example, an integrated computational element (ICE). The electromagnetic radiation that optically interacts with the processing element is changed so as to be readable by a detector, such that an output of the detector can be correlated to the substance or a particular characteristic thereof. The output of electromagnetic radiation from the processing element can be reflected electromagnetic radiation, transmitted electromagnetic radiation, and/or dispersed electromagnetic radiation. In addition, emission and/or scattering of the fluid or a phase thereof, for example via fluorescence, luminescence, Raman, Mie, and/or Raleigh scattering, can also be monitored by the optical computing devices.

As used herein, the term "substance," or variations thereof, refers to a buoyant matter or material of interest to be tested or otherwise evaluated using an optical computing device, as described herein. In keeping with Archimedes' principle, the substance is considered "buoyant" in the sense that it is generally buoyed up by a force equal to the weight of a surrounding fluid displaced by the substance. In the present disclosure, the surrounding fluid includes the fluid disposed within the work string 114 or the flow path 204. The substance may include a characteristic of interest, as defined below, and may be any fluid or any solid substance or material that is buoyant and therefore configured to float in the direction of the optical computing device 128 of FIG. 1 upon release from its respective indicator chamber 222 (FIGS. 2A-2B).

In one or more embodiments, the substance may be entrained in the fluid disposed within the work string 114 and/or the flow path 204. For instance, when a substance is entrained in the fluid, the hydraulic forces acting on the substance cause the substance to move with the fluid flow. The propensity for a substance to be entrained in the fluid depends on the shape of the substance (or particles which make up the substance), the viscosity of the fluid, the relative density between the fluid and the substance, and the likelihood for the substance to be dissolved within or by the fluid. In some embodiments, a substance may be entrained in the fluid without being more strictly buoyant than the fluid. In other words, the substance may be conveyed or otherwise flowed to the surface 104 by being either entrained in the fluid or otherwise buoyant with respect to the fluid, or a combination of the two.

As used herein, the term "fluid" refers to any substance that is capable of flowing, including particulate solids, liquids, gases, slurries, emulsions, powders, muds, glasses, mixtures, combinations thereof, and the like. The fluid may be a single phase or a multiphase fluid. In some embodiments, the fluid can be an aqueous fluid, including water, brines, or the like. In other embodiments, the fluid may be a non-aqueous fluid, including organic compounds, more specifically, hydrocarbons, oil, a refined component of oil, petrochemical products, and the like. In some embodiments, the fluid can be a treatment fluid, a fracturing fluid, or a formation fluid as found in the oil and gas industry. The fluid may also include any alcohols, esters, sugars, paints, waxes, combinations thereof, and the like. The fluid may also have one or more solids or solid particulate substances entrained therein. For instance, fluids can include various flowable mixtures of solids, liquids and/or gases. Illustrative gases that can be considered fluids according to the present embodiments, include, for example, air, nitrogen, carbon dioxide, argon, helium, methane, ethane, butane, and other hydrocarbon gases, combinations thereof, and/or the like.

As used herein, the term "characteristic" refers to a chemical, mechanical, or physical property of a substance (i.e., the substance 224), such as a buoyant fluid or solid. A characteristic may also refer to a chemical, mechanical, or physical property of a phase of the substance. Illustrative characteristics of the substance that can be detected or otherwise monitored with the optical computing devices disclosed herein can include, for example, chemical composition (e.g., identity and concentration in total or of individual components), phase presence, impurity content, pH, viscosity, density, ionic strength, total dissolved solids, salt content, porosity, opacity, bacteria content, concentrations thereof, combinations thereof, color, state of matter (e.g., solid, liquid, gas, emulsion, mixtures, etc.), and the like. Other exemplary characteristics can include volumetric flow rate or mass flow rate.

As used herein, the term "flow path" refers to a route through which a substance is capable of being transported between two points. In some cases, the flow path need not be continuous or otherwise contiguous between the two points. Exemplary flow paths include, but are not limited to, a flowline, a pipeline, a production tubular or tubing, a work string, an annulus defined between a wellbore and a pipeline, a hose, a process facility, a storage vessel, a tanker, a railway tank car, a transport ship or vessel, a subterranean formation, combinations thereof, or the like. In cases where the flow path is a pipeline or the like, the pipeline may be a pre-commissioned pipeline or an operational pipeline. In other cases, the flow path may be created or generated via movement of an optical computing device through a fluid (e.g., an open air sensor). In yet other cases, the flow path is not necessarily contained within any rigid structure, but refers to the path fluid takes between two points, such as where a fluid flows from one location to another without being contained, per se. It should be noted that the term "flow path" does not necessarily imply that a fluid is flowing therein, rather that a fluid is capable of being transported or otherwise flowable therethrough.

As used herein, the term "electromagnetic radiation" refers to radio waves, microwave radiation, infrared and near-infrared radiation, visible light, ultraviolet light, X-ray radiation and gamma ray radiation.

As used herein, the term "optically interact" or variations thereof refers to the reflection, transmission, scattering, diffraction, or absorption of electromagnetic radiation either on, through, or from one or more processing elements (i.e., integrated computational elements) or a substance. Accordingly, optically interacted light refers to electromagnetic radiation that has been reflected, transmitted, scattered, diffracted, or absorbed by, emitted, or re-radiated, for example, using an integrated computational element, but may also apply to interaction with a substance.

Figure 3:
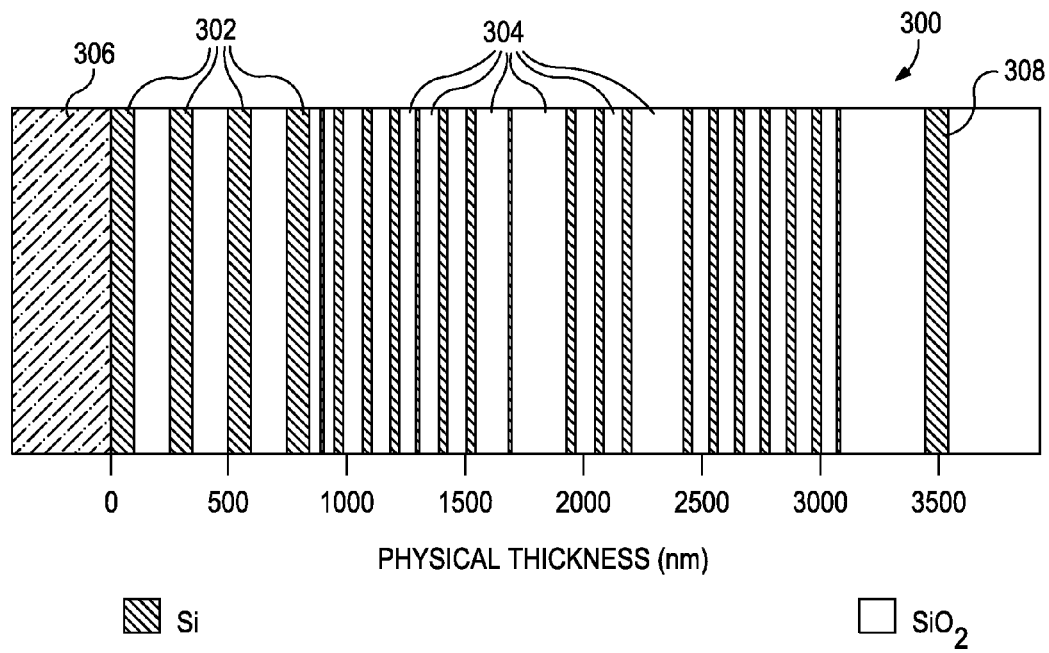
FIG. 3 illustrates an exemplary integrated computation element, according to one or more embodiments.

As mentioned above, the processing element used in the exemplary optical computing device 128 may be an integrated computational element (ICE). In operation, an ICE component is capable of distinguishing electromagnetic radiation related to a substance or a characteristic thereof from electromagnetic radiation related to other components or analytes of the substance. Referring to FIG. 3, illustrated is an exemplary ICE 300, according to one or more embodiments. As illustrated, the ICE 300 may include a plurality of alternating layers 302 and 304, such as silicon (Si) and $SiO_2$ (quartz), respectively. In general, these layers 302, 304 consist of materials whose index of refraction is high and low, respectively. Other examples of materials might include niobia and niobium, germanium and germania, MgF, SiO, and other high and low index materials known in the art. The layers 302, 304 may be strategically deposited on an optical substrate 306. In some embodiments, the optical substrate 306 is BK-7 optical glass. In other embodiments, the optical substrate 306 may be another type of optical substrate, such as quartz, sapphire, silicon, germanium, zinc selenide, zinc sulfide, or various plastics such as polycarbonate, polymethylmethacrylate (PMMA), polyvinylchloride (PVC), diamond, ceramics, combinations thereof, and the like.

At the opposite end (e.g., opposite the optical substrate 306 in FIG. 3), the ICE 300 may include a layer 308 that is generally exposed to the environment of the device or installation and able to optically interact with electromagnetic radiation or the substance 224 (FIGS. 2A-2B). The number of layers 302, 304 and the thickness of each layer 302, 304 are determined from the spectral attributes acquired from a spectroscopic analysis of a characteristic of the substance being analyzed using a conventional spectroscopic instrument. It should be understood that the exemplary ICE 300 in FIG. 3 does not in fact represent any particular characteristic of a given substance, but is provided for purposes of illustration only. Consequently, the number of layers 302, 304 and their relative thicknesses, as shown in FIG. 3, bear no correlation to any particular characteristic. Moreover, those skilled in the art will readily recognize that the materials that make up each layer 302, 304 (i.e., Si and $SiO_2$) may vary, depending on the application, cost of materials, and/or applicability of the material to the given substance being analyzed.

In some embodiments, the material of each layer 302, 304 can be doped or two or more materials can be combined in a manner to achieve the desired optical characteristic. In addition to solids, the exemplary ICE 300 may also contain liquids and/or gases, optionally in combination with solids, in order to produce a desired optical characteristic. In the case of gases and liquids, the ICE 300 can contain a corresponding vessel (not shown), which houses the gases or liquids. Exemplary variations of the ICE 300 may also include holographic optical elements, gratings, piezoelectric, light pipe, and/or acousto-optic elements, for example, that can create transmission, reflection, and/or absorptive properties of interest.

The multiple layers 302, 304 exhibit different refractive indices. By properly selecting the materials of the layers 302, 304 and their relative thickness and spacing, the ICE 300 may be configured to selectively pass/reflect/refract predetermined fractions of electromagnetic radiation at different wavelengths. Each wavelength is given a predetermined weighting or loading factor. The thickness and spacing of the layers 302, 304 may be determined using a variety of approximation methods from the spectrum of the characteristic or analyte of interest. These methods may include inverse Fourier transform (IFT) of the optical transmission spectrum and structuring the ICE 300 as the physical representation of the IFT. The approximations convert the IFT into a structure based on known materials with constant refractive indices. Further information regarding the structures and design of exemplary ICE elements is provided in *Applied Optics*, Vol. 35, pp. 5484-5492 (1996) and Vol. 29, pp. 2876-2893 (1990), which are hereby incorporated by reference.

The weightings that the layers 302, 304 of the ICE 300 apply at each wavelength are set to the regression weightings described with respect to a known equation, or data, or spectral signature. When electromagnetic radiation interacts with a substance, unique physical and chemical information about the substance may be encoded in the electromagnetic radiation that is reflected from, transmitted through, or otherwise radiated from the substance. This information is often referred to as the spectral "fingerprint" of the substance. The ICE 300 may be configured to perform the dot product of the electromagnetic radiation received by the ICE 300 and the wavelength dependent transmission function of the ICE 300. The wavelength dependent transmission function of the ICE is dependent on the layer material refractive index, the number of layers 302, 304 and the layer thicknesses. The ICE 300 transmission function is then analogous to a desired regression vector derived from the solution to a linear multivariate problem targeting a specific component of the sample substance being analyzed. As a result, the output light intensity of the ICE 300 is related to the characteristic or analyte of interest.

Optical computing devices employing such an ICE may be capable of extracting the information of the spectral fingerprint of multiple characteristics or analytes within a substance and converting that information into a detectable output regarding the overall properties of the substance. That is, through suitable configurations of the optical computing devices, electromagnetic radiation associated with characteristics or analytes of interest in a substance can be separated from electromagnetic radiation associated with all other components of the substance in order to estimate the properties of the substance in real-time or near real-time. Further details regarding how the exemplary ICE 300 is able to distinguish and process electromagnetic radiation related to the characteristic or analyte of interest are described in U.S. Pat. Nos. 6,198,531; 6,529,276; and 7,920,258, incorporated herein by reference in their entirety.

Figure 4:
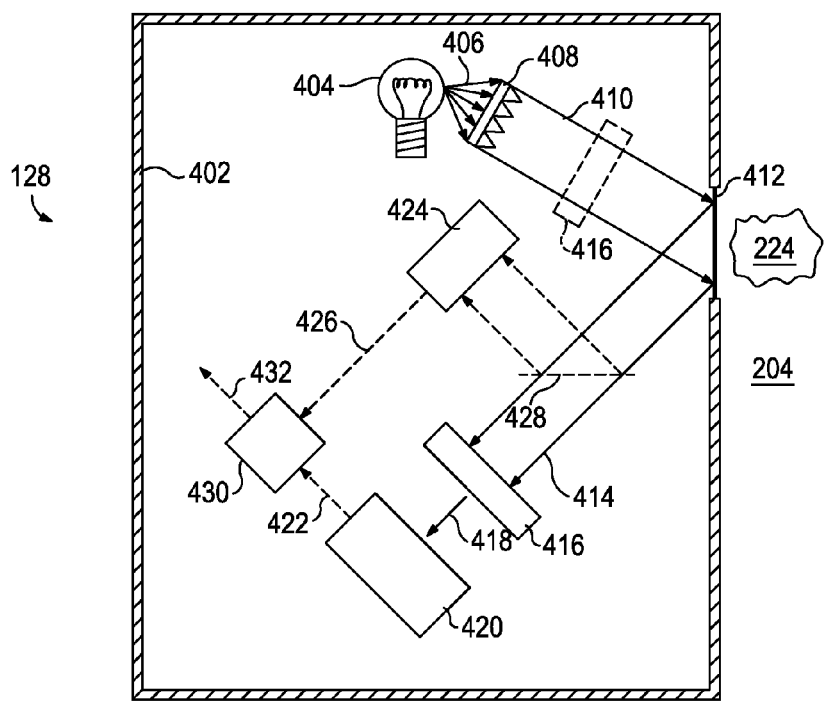
FIG. 4 is a schematic diagram of an exemplary optical computing device, according to one or more embodiments.

Referring now to FIG. 4, with reference to FIGS. 1, 2A, and 2B, illustrated is a schematic view of an exemplary optical computing device, such as the optical computing device 128 of FIG. 1, according to one or more embodiments. Those skilled in the art will readily appreciate that the optical computing device 128, and its components described below, are not necessarily drawn to scale nor, strictly speaking, depicted as optically correct as understood by those skilled in optics. Instead, FIG. 4 is merely illustrative in nature and used generally herein in order to supplement understanding of the description of the various exemplary embodiments. Nonetheless, while FIG. 4 may not be optically accurate, the conceptual interpretations depicted therein accurately reflect the exemplary nature of the various embodiments disclosed.

As briefly described above, the optical computing device 128 may be arranged or otherwise configured to monitor the flow path 204 of the work string 114 (FIGS. 2A and 2B) and detect a substance 224 or a particular characteristic thereof. As discussed above, the substance 224 may be a buoyant material or matter able to float toward the surface 104 (FIG. 1) after it is released from its corresponding indicator chamber 222 in the downhole tool 126 (FIGS. 2A and 2B). In some embodiments, the substance 224 may be a fluid, but in other embodiments the substance 224 may be a solid or solid particulates entrained in a fluid.

As illustrated, the optical computing device 128 may be housed within a casing or housing 402 configured to substantially protect the internal components of the optical computing device 128 from damage or contamination from the substance 224 or any other substance within the flow path 204. In some embodiments, the housing 402 may operate to mechanically couple the optical computing device 128 to the work string 114 such that it is able to monitor or otherwise optically interact with the flow path 204. The housing 402 may be coupled to the work string 114 with, for example, mechanical fasteners, brazing or welding techniques, adhesives, magnets, combinations thereof, or the like. The housing 402 may be designed to withstand the pressures that may be experienced downhole and thereby provide a fluid tight seal against external contamination.

The optical computing device 128 may include an electromagnetic radiation source 404 configured to emit or otherwise generate electromagnetic radiation 406. The electromagnetic radiation source 404 may be any device capable of emitting or generating electromagnetic radiation, as defined herein. For example, the electromagnetic radiation source 404 may be a light bulb, a light emitting diode (LED), a laser, a blackbody, a photonic crystal, an X-Ray source, combinations thereof, or the like. In some embodiments, a lens 408 may be configured to collect or otherwise receive the electromagnetic radiation 406 and direct a beam 410 of the electromagnetic radiation 406 toward a location for sampling or otherwise monitoring the flow path 204 and the substance 224. The lens 408 may be any type of optical device configured to convey the electromagnetic radiation 406 as desired and may include, for example, a normal lens, a Fresnel lens, a diffractive optical element, a holographic graphical element, a mirror (e.g., a focusing mirror), a type of collimator, or any other electromagnetic radiation transmitting device known to those skilled in art. In other embodiments, the lens 408 may be omitted from the optical computing device 128 and the electromagnetic radiation 406 may instead be directed toward the substance 224 directly from the electromagnetic radiation source 404. In yet other embodiments, an optical light pipe (e.g., a fiber optic cable or line) may be used to convey the electromagnetic radiation 406. As will be appreciated, the use of optical light pipes may allow the optical computing device 128 to be placed further into the formation 108.

In one or more embodiments, the optical computing device 128 may also include a sampling window 412 arranged adjacent to or otherwise in contact with the flow path 204 on one side for detection purposes. The sampling window 412 may be made from a variety of transparent, rigid or semi-rigid materials that are configured to allow transmission of the electromagnetic radiation 406 therethrough. For example, the sampling window 412 may be made of, but is not limited to, glasses, plastics, semi-conductors, crystalline materials, polycrystalline materials, hot or cold-pressed powders, combinations thereof, or the like.

After passing through the sampling window 412, the electromagnetic radiation 406 impinges upon and optically interacts with the substance 224 in the flow path 204. As a result, optically interacted radiation 414 is generated by and reflected from the substance 224. Those skilled in the art, however, will readily recognize that alternative variations of the optical computing device 128 may allow the optically interacted radiation 414 to be generated by being transmitted through, scattered or diffracted by, absorbed, emitted from, or re-radiated by and/or from the substance 224, without departing from the scope of the disclosure.

The optically interacted radiation 414 generated by the interaction with the substance 224 may be directed to or otherwise be received by an ICE 416 arranged within the optical computing device 128. The ICE 416 may be a spectral component substantially similar to the ICE 300 described above with reference to FIG. 3. Accordingly, in operation the ICE 416 may be configured to receive the optically interacted radiation 414 and produce modified electromagnetic radiation 418 corresponding to a particular characteristic of the substance 224. In particular, the modified electromagnetic radiation 418 is electromagnetic radiation that has optically interacted with the ICE 416, whereby an approximate mimicking of the regression vector corresponding to the characteristic of interest is obtained.

It should be noted that, while FIG. 4 depicts the ICE 416 as receiving reflected electromagnetic radiation from the substance 224, the ICE 416 may be arranged at any point along the optical train of the optical computing device 128, without departing from the scope of the disclosure. For example, in one or more embodiments, the ICE 416 (as shown in dashed) may be arranged within the optical train prior to the sampling window 412 and equally obtain substantially the same results. In other embodiments, the sampling window 412 may serve a dual purpose as both a transmission window and the ICE 416 (i.e., a spectral component). In yet other embodiments, the ICE 416 may generate the modified electromagnetic radiation 418 through reflection, instead of transmission therethrough.

Moreover, while only one ICE 416 is shown in the optical computing device 128, embodiments are contemplated herein which include the use of two or more ICE components in the optical computing device 128 in order to monitor more than one characteristic of the substance 224 at a given time. In such embodiments, various configurations for multiple ICE components can be used, where each ICE component is configured to detect a particular and/or distinct characteristic of interest. In some embodiments, the characteristic can be analyzed sequentially using the multiple ICE components that are provided a single beam of electromagnetic radiation that is reflected from or transmitted through the substance 224. In some embodiments, multiple ICE components can be arranged on a rotating disc where the individual ICE components are only exposed to the beam of electromagnetic radiation for a short time. Advantages of this approach can include the ability to analyze multiple characteristics of the substance 224 using a single optical computing device and the opportunity to assay additional characteristics simply by adding additional ICE components to the rotating disc. These optional embodiments employing two or more ICE components are further described in co-pending U.S. patent application Ser. Nos. 13/456,264, 13/456,405, 13/456,302, and 13/456,327, the contents of which are hereby incorporated by reference in their entireties.

In other embodiments, multiple optical computing devices 128 can be used at a single location (or at least in close proximity) along the flow path 204, where each optical computing device 128 contains a unique ICE component that is configured to detect a particular characteristic of interest. Each optical computing device 128 can be coupled to a corresponding detector or detector array that is configured to detect and analyze an output of electromagnetic radiation from the respective optical computing device 128. Parallel configurations of optical computing devices 128 can be particularly beneficial for applications that require low power inputs and/or no moving parts.

The modified electromagnetic radiation 418 generated by the ICE 416 may subsequently be conveyed to a detector 420 for quantification of the signal. The detector 420 may be any device capable of detecting electromagnetic radiation, and may be generally characterized as an optical transducer. In some embodiments, the detector 420 may be, but is not limited to, a thermal detector such as a thermopile or photoacoustic detector, a semiconductor detector, a piezo-electric detector, a charge coupled device (CCD) detector, a video or array detector, a split detector, a photon detector (such as a photomultiplier tube), photodiodes, combinations thereof, or the like, or other detectors known to those skilled in the art.

In some embodiments, the detector 420 may be configured to produce an output signal 422 in real-time or near real-time in the form of a voltage (or current) that corresponds to the particular characteristic of interest in the substance 224. The voltage returned by the detector 420 is essentially the dot product of the optical interaction of the optically interacted radiation 414 with the respective ICE 416 as a function of the concentration of the characteristic of interest of the substance 224. As such, the output signal 422 produced by the detector 420 and the concentration of the characteristic of interest in the substance 224 may be related, for example, directly proportional. In other embodiments, however, the relationship may correspond to a polynomial function, an exponential function, a logarithmic function, and/or a combination thereof.

In some embodiments, the optical computing device 128 may include a second detector 424, which may be similar to the first detector 420 in that it may be any device capable of detecting electromagnetic radiation. The second detector 424 may be used to detect radiating deviations stemming from the electromagnetic radiation source 404. Undesirable radiating deviations can occur in the intensity of the electromagnetic radiation 406 due to a wide variety of reasons and potentially causing various negative effects on the optical computing device 128. These negative effects can be particularly detrimental for measurements taken over a period of time. In some embodiments, radiating deviations can occur as a result of a build-up of film or material on the sampling window 412 which has the effect of reducing the amount and quality of light ultimately reaching the first detector 420. Without proper compensation, such radiating deviations could result in false readings and the output signal 422 would no longer be primarily or accurately related to the characteristic of interest.

To compensate for these types of undesirable effects, the second detector 424 may be configured to generate a compensating signal 426 generally indicative of the radiating deviations of the electromagnetic radiation source 404, and thereby normalize the output signal 422 generated by the first detector 420. As illustrated, the second detector 424 may be configured to receive a portion of the optically interacted radiation 414 via a beamsplitter 428 in order to detect the radiating deviations. In other embodiments, however, the second detector 424 may be arranged to receive electromagnetic radiation from any portion of the optical train in the optical computing device 128 in order to detect the radiating deviations, without departing from the scope of the disclosure.

In some applications, the output signal 422 and the compensating signal 426 may be conveyed to or otherwise received by a signal processor 430 communicably coupled to both the detectors 420, 424. The signal processor 430 may be a computer including a non-transitory machine-readable medium, and may be configured or otherwise programmed to computationally combine the compensating signal 426 with the output signal 422 in order to normalize the output signal 422 in view of any radiating deviations detected by the second detector 424. In some embodiments, computationally combining the output and compensating signals 422, 426 may entail computing a ratio of the two signals 422, 426.

In real-time or near real-time, the signal processor 430 may be configured to determine or otherwise calculate the concentration or magnitude of the characteristic of interest in the substance 224. In some embodiments, the signal processor 430 may be programmed to recognize whether the detected concentration of the substance 224 or a characteristic thereof falls within or without a predetermined or preprogrammed range for its intended purpose as used in conjunction with the downhole tool 126. For example, the signal processor 430 may be programmed such that when the concentration of the substance 224 or a characteristic thereof remains below a minimum predetermined limit, the signal processor 430 does not act. In contrast, when the concentration of the substance 224 or a characteristic thereof reaches or otherwise surpasses the minimum predetermined limit, the signal processor 430 may be configured to send a signal 432 to the computer system 130 (FIG. 1) in order to inform the well operator that the sleeve 210 has been effectively opened. As briefly described above, the signal 432 may be conveyed to the computer system 130 via the communication line 132.

Those skilled in the art will readily recognize the several advantages that the disclosed systems and methods may provide. For example, referring again to FIGS. 1, 2A, and 2B, with continued reference to FIG. 4, in at least one embodiment, a predetermined amount or concentration of the buoyant substance 224 or a predetermined concentration of a characteristic of the substance 224 may be retained within the indictor chamber 222 when the sleeve 210 is in the closed configuration. In some embodiments, the buoyant substance 224 may be a fluid, such as non-aqueous fluids, hydrocarbons, oil, a refined component of oil, petrochemical products, organic compounds, alcohols, esters, sugars, paints, waxes, combinations thereof, and the like. In other embodiments, the substance 224 may be a gaseous fluid such as, but not limited to, air, nitrogen, carbon dioxide, argon, helium, methane, ethane, butane, and other hydrocarbon gases. In yet other embodiments, the substance 224 may be a solid material such as, but not limited to, plastics, elastomers, syntactic foams, gas-filled metals, gas-filled ceramics, gas-filled glasses, composite materials and/or structures, thermoplastics, thermoset materials, combinations thereof, and the like. As will be appreciated, such "gas-filled" solids may be filled with any gas, such as, but not limited to, air, nitrogen, carbon dioxide, argon, helium, methane, ethane, butane, other hydrocarbon gases, combinations thereof, and the like.

Once the sleeve 210 is moved to the open configuration, as generally described above, the buoyant substance 224 may escape the indicator chamber 222 into the flow path 204 and proceed to float toward the surface 104. At or near the surface 104, the substance 224 (or a characteristic thereof) may be detected by the optical computing device 128. When the predetermined minimum limit of the substance 224 is met or surpassed, the optical computing device 128 may be configured to send the signal 432 to the computer system 130 and thereby provide a positive indication that the sleeve 210 has indeed moved into the open configuration. Upon recognizing that the sleeve 210 is in fact in the open configuration, a well operator may confidently proceed with subsequent well operations that require the sleeve 210 to be in such a position.

Referring particularly to FIG. 1, in some embodiments, each downhole tool 126*a*-*c* may retain or otherwise include a unique substance 224 maintained within a corresponding indicator chamber 222. In such embodiments, the optical computing device 128, or a plurality of optical computing devices 128, may be configured to detect each unique substance 224 and convey corresponding signals 432 to the computer system 130. For example, when the substance 224 corresponding to the first downhole tool 126*a* is detected, the signal 432 may be an indication that the sleeve 210 associated with the first downhole tool 126*a* has moved into its open configuration. Similarly, when the substance 224 corresponding to the second downhole tool 126*b* is detected, the signal 432 may be an indication that the sleeve 210 associated with the second downhole tool 126*b* has moved into its open configuration. Lastly, when the substance 224 corresponding to the third downhole tool 126*c* is detected, the signal 432 may be an indication that the sleeve 210 associated with the third downhole tool 126*c* has moved into its open configuration.

Those skilled in the art will readily appreciate the advantages this may provide, especially as employed in the performance of wellbore servicing operations. For example, having a positive indication that a sleeve 210 for a particular downhole tool 126*a*-*c* is in fact opened may allow the well operator to ascertain the configuration of such downhole tools 126*a*-*c* while the particular downhole tool 126*a*-*c* remains downhole. As such, the operator can be assured that a given servicing fluid will be communicated to a given pay zone within the subterranean formation 108. Moreover, such assurances may allow the operator to avoid mistakes in the performance of various servicing operations, for example, communicating a given fluid to the wrong pay zone. In addition, the operator can perform servicing operations with the confidence that the operation is, in fact, reaching the intended pay zone.

In some embodiments, the optical computing device 128 may have more than one ICE 416 configured to monitor or otherwise detect a corresponding more than one substance 224. For example, in at least one embodiment, a first ICE may be configured to detect the substance 224 while a second ICE may be configured to detect a fluid (e.g., water, a production fluid, a hydrocarbon, etc.) that entrains the substance 224. In such embodiments, the signal processor 430 may be configured to calculate a ratio between the two detected materials in order to determine when the detected concentration of the substance 224 or a characteristic thereof falls within or without the predetermined or preprogrammed range for its intended purpose as used in conjunction with the downhole tool 126. As will be appreciated, the ratio between the two detected materials may also help control for optical intensity and detect occlusion of the sampling window 412.

In other embodiments, two or more different substances 224 may be released from a single location within the work string 114 and the ratio between the two dissimilar substances 224, as measured by the optical computing device 128, may be an indicator or otherwise identify the originating location of the substances 224. As a result, an operator may be informed in real-time that the downhole tool 126 at that location was effectively actuated.

In some embodiments, the downhole tool 126 may be a fluid sampling device or the like and the embodiments discussed herein may be advantageous in determining whether the device has been effectively actuated or whether a sample has indeed been obtained. One of the concerns in fluid sampling is exactly when a sample is taken. Positive verification of the sampling may prove advantageous in showing the behavior of the sampled fluid at the surface 104. For instance, the difference between the fluid sampled downhole (and kept under pressure) and the fluid produced at the surface 104 (and not kept under pressure) may provide an operator with several properties of the sample fluid. It would also help in recognizing and extrapolation between the properties as measured at the surface 104 and the actual downhole properties of the sampled fluid.

In other embodiments, the downhole tool 126 may be a valve (i.e., any flow restriction devices such as inflow control devices, autonomous inflow control devices, chokes, and the like) arranged within the work string 114 or otherwise within the wellbore 106 and the embodiments discussed herein may be advantageous in determining or otherwise sensing the position of the valve. For instance, as the valve is actuated or otherwise moved between open and closed positions, the substance 224 may be released into the flow path 204 and detectable by the optical computing device 128 at or near the surface 104. Verifying that the valve has indeed shifted or otherwise moved to its intended position may prove advantageous since, as will be recognized by those skilled in the art, it is often difficult to know whether downhole valves or restriction devices have actually moved as intended.

In yet other embodiments, the downhole tool 126 may be a multi-shift tool, such as a tool with a j-slot mechanism, and the embodiments discussed herein may be advantageous in determining or otherwise sensing the position of the tool. For instance, the tool may be configured to release the substance 224 into the flow path 204 once moved to a particular configuration. In at least one embodiment, detecting or otherwise sensing the substance 224 at or near the surface 104 with the optical computing device 128 may inform an operator that the tool is preparing to act, such as by releasing a valve or opening a plug.

In other embodiments, the substance 224 may be entrained within an injection fluid or the like during a formation stimulation operation, such as a hydraulic fracturing and gravel packing process. Accordingly, once the formation stimulation operation is complete, the substance 224 will be effectively injected into or otherwise reside within the formation 108. During production operations, the substance 224 may be produced with the normal flow of fluids, such as hydrocarbons and water, and subsequently detected at or near the surface 104 with the optical computing device 128. As a result, an operator may be apprised in real-time that the particular pay zone is producing. In at least one embodiment, dissimilar substances 224 or substances 224 exhibiting a different characteristic may be entrained within injection fluids directed to different pay zones within the formation 108. Upon detecting such dissimilar substances 224 at the surface 104 with the optical computing device 128, an operator may be apprised in real-time as to which pay zone is producing.

In one or more embodiments, rather than being released into the flow path 204 formed within the work string 114, the substance 224 may be released or otherwise conveyed into the annulus 124 (FIG. 1) during an injection operation in order to detect the actuation or operation of the downhole tool 126. As will be appreciated, releasing the substance 224 into the annulus 124 may remove entrainment forces that would otherwise act on the substance 224, thereby allowing buoyancy of the substance 224 to dominate the movement of the substance 224 toward the optical computing device 128 at or near the surface 104. Once the substance 224 is detected by the optical computing device 128, an operator may be apprised in real-time of the successful actuation or operation of the downhole tool 126.

It is recognized that the various embodiments herein directed to computer control and/or artificial neural networks, including various blocks, modules, elements, components, methods, and algorithms, can be implemented using computer hardware, software, combinations thereof, and the like. To illustrate this interchangeability of hardware and software, various illustrative blocks, modules, elements, components, methods and algorithms have been described generally in terms of their functionality. Whether such functionality is implemented as hardware or software will depend upon the particular application and any imposed design constraints. For at least this reason, it is to be recognized that one of ordinary skill in the art can implement the described functionality in a variety of ways for a particular application. Further, various components and blocks can be arranged in a different order or partitioned differently, for example, without departing from the scope of the embodiments expressly described.

Computer hardware used to implement the various illustrative blocks, modules, elements, components, methods, and algorithms described herein can include a processor configured to execute one or more sequences of instructions, programming stances, or code stored on a non-transitory, computer-readable medium. The processor can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network, or any like suitable entity that can perform calculations or other manipulations of data. In some embodiments, computer hardware can further include elements such as, for example, a memory (e.g., random access memory (RAM), flash memory, read only memory (ROM), programmable read only memory (PROM), erasable read only memory (EPROM)), registers, hard disks, removable disks, CD-ROMs, DVDs, or any other like suitable storage device or medium.

Executable sequences described herein can be implemented with one or more sequences of code contained in a memory. In some embodiments, such code can be read into the memory from another machine-readable medium. Execution of the sequences of instructions contained in the memory can cause a processor to perform the process steps described herein. One or more processors in a multi-processing arrangement can also be employed to execute instruction sequences in the memory. In addition, hard-wired circuitry can be used in place of or in combination with software instructions to implement various embodiments described herein. Thus, the present embodiments are not limited to any specific combination of hardware and/or software.

As used herein, a machine-readable medium will refer to any non-transitory medium that directly or indirectly provides instructions to a processor for execution. A machine-readable medium can take on many forms including, for example, non-volatile media, volatile media, and transmission media. Non-volatile media can include, for example, optical and magnetic disks. Volatile media can include, for example, dynamic memory. Transmission media can include, for example, coaxial cables, wire, fiber optics, and wires that form a bus. Common forms of machine-readable media can include, for example, floppy disks, flexible disks, hard disks, magnetic tapes, other like magnetic media, CD-ROMs, DVDs, other like optical media, punch cards, paper tapes and like physical media with patterned holes, RAM, ROM, PROM, EPROM and flash EPROM.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

The invention claimed is:

1. A well system, comprising:
a work string defining a flow path therein;
a downhole tool coupled to the work string and having a body that defines an interior in fluid communication with and extending from the flow path;
an indicator chamber defined in an inner surface of the body to retain a substance until the downhole tool is actuated, whereupon the indicator chamber becomes exposed to the interior and the substance is released into the flow path via the interior; and
an optical computing device in optical communication with the flow path for detecting a characteristic of the substance in the flow path and communicating a signal when the characteristic is detected, the signal being indicative that the downhole tool has been actuated.

2. The well system of claim 1, wherein the optical computing device comprises:
at least one integrated computational element configured to optically interact with the substance and thereby generate optically interacted light; and
at least one detector arranged to receive the optically interacted light and generate an output signal corresponding to the characteristic of the substance.

3. The well system of claim 1, wherein the substance is buoyant as compared to fluids disposed within the flow path.

4. The well system of claim 1, wherein the substance is entrained within the fluids disposed within the flow path.

5. The well system of claim 3, wherein the optical computing device is arranged at or near a well surface and the substance is configured to float towards the optical computing device within the flow path after being released from the indicator chamber.

6. The well system of claim 1, wherein the substance is a fluid selected from the group consisting of hydrocarbons, oil, a refined component of oil, petrochemical products, organic compounds, air, nitrogen, carbon dioxide, argon, helium, methane, ethane, butane, hydrocarbon gases, alcohols, esters, sugars, paints, waxes and combinations thereof.

7. The well system of claim 6, wherein the characteristic is a predetermined concentration of the fluid.

8. The well system of claim 1, wherein the substance is a solid selected from the group consisting of plastics, elastomers, syntactic foams, gas-filled metals, gas-filled ceramics, gas-filled glasses, composite materials and/or structures, thermoplastics, thermoset materials, and combinations thereof.

9. The well system of claim 1, wherein the characteristic of the substance is at least one of a chemical composition, a phase, an impurity content, a pH level, a viscosity, a density, a total dissolved solids concentration, a salt content, a porosity, an opacity, a bacteria content, a color, and a state of matter.

10. A method, comprising:
retaining a substance within an indicator chamber defined in an inner surface of a body of a downhole tool, the downhole tool being coupled to a work string that defines a flow path and the body defining an interior in fluid communication with and extending from the flow path;
actuating the downhole tool and thereby exposing the indicator chamber and releasing the substance into the flow path via the interior;
monitoring the flow path with an optical computing device configured to detect a characteristic of the substance in the flow path; and
communicating a signal with the optical computing device when the characteristic of the substance is detected, the signal being indicative that the downhole tool has been actuated.

11. The method of claim 10, wherein monitoring the flow path with the optical computing device comprises:
optically interacting at least one integrated computational element with the substance to generate optically interacted light;
receiving the optically interacted light with at least one detector; and
generating an output signal with the at least one detector corresponding to the characteristic of the substance.

12. The method of claim 10, wherein communicating the signal with the optical computing device comprises communicating the signal to a computer system arranged at a well surface.

13. The method of claim 10, wherein the substance is buoyant as compared to fluids disposed within the flow path and the optical computing device is arranged at or near a well surface, the method further comprising floating the substance towards the optical computing device within the flow path after being released from the indicator chamber.

14. The method of claim 13, wherein the substance is a fluid selected from the group consisting of hydrocarbons, oil, a refined component of oil, petrochemical products, organic compounds, air, nitrogen, carbon dioxide, argon, helium, methane, ethane, butane, hydrocarbon gases, alcohols, esters, sugars, paints, waxes, and combinations thereof.

15. The method of claim 10, further comprising:
entraining the substance within a fluid within the flow path;
monitoring the flow path with the optical computing device for the fluid; and
calculating a ratio between the fluid and the substance with the optical computing device.

16. A well system, comprising:
a work string defining a flow path therein;
a sliding sleeve assembly coupled to the work string and having a body with a sleeve arranged within an interior of the body, the interior being in fluid communication with and extending from the flow path and the sleeve being movable between a closed configuration, where fluid communication is prevented between the interior of the body and an exterior of the work string, and an open configuration, where fluid communication is allowed between the interior and the exterior;
an indicator chamber defined in an inner surface of the body to retain a substance when the sleeve is in the closed configuration and release the substance into the flow path via the interior when the sleeve is in the open configuration; and
an optical computing device in optical communication with the flow path to detect a characteristic of the substance in the flow path and communicate a signal when the characteristic is detected, the signal being indicative that the sleeve is in the open configuration.

17. The well system of claim 16, wherein the optical computing device comprises:
   at least one integrated computational element configured to optically interact with the substance and thereby generate optically interacted light; and
   at least one detector arranged to receive the optically interacted light and generate an output signal corresponding to the characteristic of the substance.

18. The well system of claim 16, wherein the substance is buoyant as compared to fluids disposed within the flow path.

19. The well system of claim 18, wherein the optical computing device is arranged at or near a well surface and the substance is configured to float towards the optical computing device within the flow path after being released from the indicator chamber.

20. The well system of claim 16, wherein the substance is a fluid selected from the group consisting of hydrocarbons, oil, a refined component of oil, petrochemical products, organic compounds, air, nitrogen, carbon dioxide, argon, helium, methane, ethane, butane, hydrocarbon gases, alcohols, esters, sugars, paints, waxes, and combinations thereof.

21. The well system of claim 20, wherein the characteristic is a predetermined concentration of the fluid.

22. The well system of claim 16, wherein the substance is a solid selected from the group consisting of plastics, elastomers, syntactic foams, gas-filled metals, gas-filled ceramics, gas-filled glasses, composite materials and/or structures, thermoplastics, thermoset materials, and combinations thereof.

23. A method, comprising:
   retaining a substance within an indicator chamber defined in an inner surface of a body of a sliding sleeve assembly, the sliding sleeve assembly being coupled to a work string that defines a flow path, and the body defining an interior in fluid communication with and extending from the flow path;
   moving a sleeve arranged within the interior from a closed configuration, where the indicator chamber is occluded and fluid communication is prevented between the interior of the body and an exterior of the work string, and an open configuration, where the indicator chamber is exposed to the interior and fluid communication is allowed between the interior and the exterior;
   releasing the substance into the flow path from the indicator chamber via the interior;
   monitoring the flow path with an optical computing device configured to detect a characteristic of the substance in the flow path; and
   communicating a signal with the optical computing device when the characteristic of the substance is detected, the signal being indicative that the sleeve is in the open configuration.

24. The method of claim 23, wherein monitoring the flow path with the optical computing device comprises:
   optically interacting at least one integrated computational element with the substance to generate optically interacted light;
   receiving the optically interacted light with at least one detector; and
   generating an output signal with the at least one detector corresponding to the characteristic of the substance.

25. The method of claim 23, wherein the substance is buoyant as compared to fluids disposed within the flow path and the optical computing device is arranged at or near a well surface, the method further comprising floating the substance towards the optical computing device within the flow path after being released from the indicator chamber.

26. The method of claim 25, wherein the substance is a fluid selected from the group consisting of hydrocarbons, oil, a refined component of oil, petrochemical products, organic compounds, air, nitrogen, carbon dioxide, argon, helium, methane, ethane, butane, hydrocarbon gases, alcohols, esters, sugars, paints, waxes, and combinations thereof.

27. The method of claim 25, wherein the substance is a solid selected from the group consisting of plastics, elastomers, syntactic foams, gas-filled metals, gas-filled ceramics, gas-filled glasses, composite materials and/or structures, thermoplastics, thermoset materials, and combinations thereof.

28. The method of claim 23, further comprising:
   entraining the substance within a fluid within the flow path;
   monitoring the flow path with the optical computing device for the fluid; and
   calculating a ratio between the fluid and the substance with the optical computing device.

* * * * *